United States Patent

Strauss et al.

[11] Patent Number: 5,158,533
[45] Date of Patent: Oct. 27, 1992

[54] COMBINED CARDIOTOMY/VENOUS/PLEURAL DRAINAGE AUTOTRANSFUSION UNIT WITH FILTER AND INTEGRAL MANOMETER AND WATER SEAL

[75] Inventors: Brian Strauss, Costa Mesa; Jack Brown, Santa Ana, both of Calif.

[73] Assignee: Gish Biomedical, Inc., Santa Ana, Calif.

[21] Appl. No.: 676,753

[22] Filed: Mar. 26, 1991

[51] Int. Cl.$^5$ .............................. A61M 1/14
[52] U.S. Cl. ............................. 604/4; 604/6; 604/403; 604/319; 604/321; 422/46; 422/47; 422/48
[58] Field of Search ...................... 604/4-6, 604/319, 321; 128/DIG. 3; 422/46-48; 210/256

[56] References Cited

U.S. PATENT DOCUMENTS

| | | | |
|---|---|---|---|
| 4,182,739 | 1/1980 | Curtis | 422/47 |
| 4,228,125 | 10/1980 | Lobdell et al. | 422/46 |
| 4,297,318 | 10/1981 | Raible | 422/46 |
| 4,737,139 | 4/1988 | Zupkas et al. | 604/4 |
| 4,818,490 | 4/1989 | Carson et al. | 422/46 |
| 4,876,066 | 10/1989 | Bringham et al. | 422/46 |
| 5,039,482 | 8/1991 | Panzani et al. | 422/46 |
| 5,043,140 | 8/1991 | Combs | 422/46 |

Primary Examiner—Robert A. Hafer
Assistant Examiner—Kerry Owens
Attorney, Agent, or Firm—George F. Bethel; Patience K. Bethel

[57] ABSTRACT

A combined cardiotomy and venous reservoir with filtration for autotransfusion of cardiotomy blood and venous blood during surgery and for postoperative wound site pleural drainage of shed blood for continued autotransfusion using the same unit. Vacuum regulation in the form of a manometer combined with a water seal are integral with the unit.

21 Claims, 6 Drawing Sheets

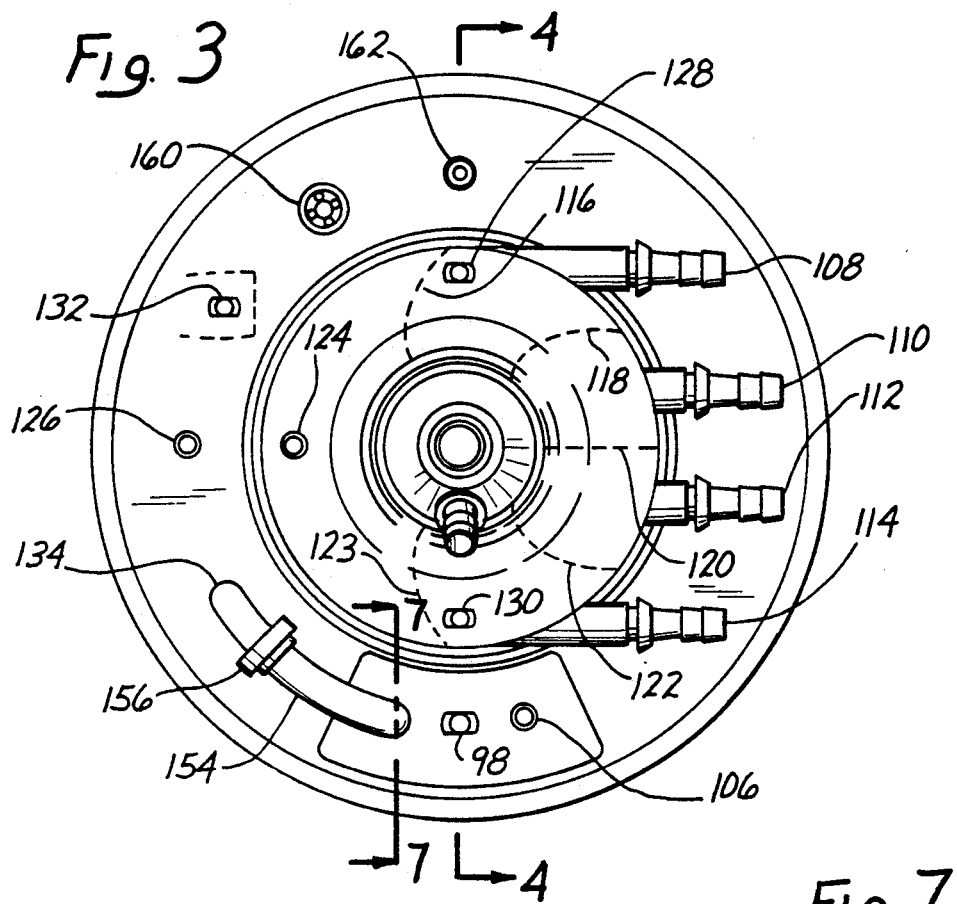
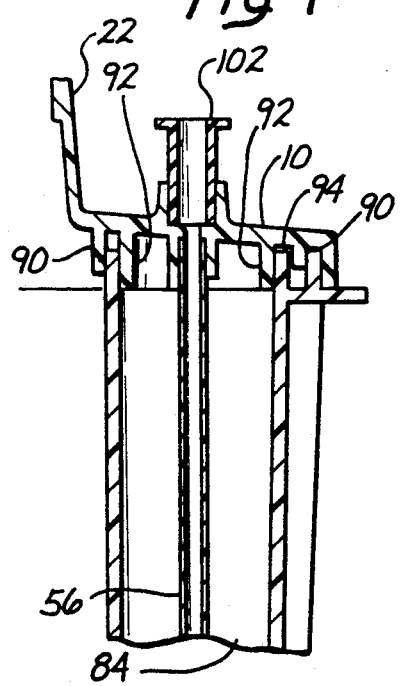
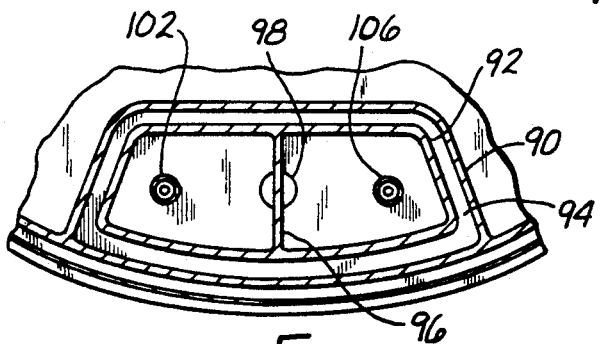
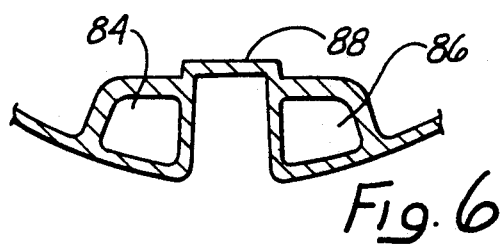

COMBINED CARDIOTOMY/VENOUS/PLEURAL DRAINAGE AUTOTRANSFUSION UNIT WITH FILTER AND INTEGRAL MANOMETER AND WATER SEAL

FIELD OF THE INVENTION

The field of this invention pertains to surgical apparatus. More particularly, it lies within the field of surgical apparatus for use in open-heart and chest cavity surgery. Such surgery can be performed utilizing oxygenators and certain reservoirs, as well as post operative devices for the patient. This invention pertains to such operation and post operative devices.

BACKGROUND OF THE INVENTION

During certain operations such as cardiopulmonary bypass operations, the function of the heart and lungs are interrupted and blood is artificially handled. The patient's body temperature is lowered and the heart itself stops beating. Circulation is maintained by withdrawal of the venous return stream through a venous cannula inserted into the right atrium, passed to a venous reservoir, passed through a blood pump (artificial heart) to a blood oxygenator (artificial lung), arterial blood filter which removes fine air bubbles and any undesirable particles that may be present in the blood before it is returned to the patient through an aortic annula.

Also, during a cardiopulmonary bypass operation, it is essential to suction away the various fluids including, for example, air, debris such as bone chips, blood, saline solution, liquids applied to the heart and the like. This must be accomplished as quickly and efficiently as possible without causing injury to the patient primarily in order to avoid damage to the heart from the fluid pressure but also to aid the surgeon.

Such fluids are termed "cardiotomy blood" which requires filtration prior to reinfusion. This term is distinguished from "shed blood" used to describe the blood accumulation which takes place after surgery and which is characterized by being of much higher quality and requiring less filtration.

Normally, a cardiotomy reservoir is used in conjunction with relatively high vacuum suction in order to remove and collect the cardiotomy blood and other liquids as quickly as possible. This vacuum can be provided through a standard air driven cardiotomy sucker through a roller pump. Use of the roller pump is clearly the method of choice since the suction can be carefully controlled and monitored.

Blood collected within a cardiotomy reservoir can be filtered and defoamed to remove air, debris and clots after which it can be reinfused to the patient. This can take place during or after surgery.

In recent years it has been found desirable during surgery to combine the cardiotomy blood with the venous blood in a single reservoir which replaces the separate cardiotomy reservoir and separate venous reservoir formerly used. This created some problems since the flow rate of venous blood is about 3 times greater than the flow of cardiotomy blood. Moreover, the venous blood is clean requiring only minimal defoaming and filtration. When venous blood was subjected to the same filtration as used for cardiotomy blood, it was found detrimental to the blood cells.

In recent years, in order to overcome this problem, separate filter chambers were provided within a single chamber to provide for separate filtering of venous blood and cardiotomy blood. Such a device is described in U.S. Pat. No. 4,642,089. This device comprises a hollow housing made of a rigid material having disposed substantially annularly a filter chamber spaced from the exterior walls of the unit. The filter chamber contains two separate chambers, an upper chamber for introduction and filtration of cardiotomy blood through a non-woven depth filter and a defoaming material and a lower chamber including a defoaming filter material but free of the non-woven depth filter.

Cardiotomy blood enters the upper filter chamber from the top of the unit and venous blood enters the lower filter chamber through the bottom of the unit. Blood entering either chamber passes through the filter and/or defoamer and is combined in a space defined by the outer walls and the filter chamber where it can be withdrawn for reinfusion to the patient.

There are several drawbacks associated with the cardiotomy/venous blood unit of U.S. Pat. No. 4,642,089. For example, venous blood, which is normally obtained by gravity flow, enters the unit from the bottom of the unit into the bottom venous chamber, where it passes through the defoaming filter prior to discharge through a bottom discharge port. The disadvantage is that this condition can lead to resistance to entry of venous blood and to discharge in the bottom leading to stasis. When the bottom or venous compartment is partially filled, the incoming venous blood must enter against this resistance. There is an inverted flow director facing downwardly within the venous chamber for direction of blood from the venous inlet toward the filter. However, this flow director is insufficient to avoid stasis. It is not good to have blood standing anywhere in the reservoir due to the formation of clots.

In U.S. Pat. No. 4,642,089, the upper cardiotomy chamber has a baffle spaced from the inlet to the cardiotomy chamber for purposes of directing the cardiotomy blood flow downwardly into the cardiotomy chamber. A flow director in the form of a truncated cone having 4 opposed fins extends the length of the cardiotomy chamber to prevent splashing and to direct the cardiotomy blood flow against the surrounding filter. The filter is comprised of a non-woven depth filter material which filters by excluding a range of size of particles and is thus only partially effective for filtration. Finally, this device does not permit postoperative drainage of shed blood or pleural drainage.

After surgery, it is desirable to provide drainage of shed blood and fluid from the area around the operative site using relatively low suction pressure as compared with the suction used for cardiotomy suction. This is a requirement to avoid injury to body tissues.

Similar low suction pressure requirements exist for pleural drainage whereby fluid, blood and gases including air are removed from the pleural space between the lungs and the rib cage to maintain the lung in the fully expanded condition. The need for pleural drainage can arise as a result of surgery, piercing of the rib cage or from illness.

In addition to low suction pressure, it is a second requirement to prevent backflow of air to the patient which could cause an emboli or introduce microorganisms into the shed blood or pleural drainage fluids to the detriment of the patient. This can happen if the vacuum is interrupted such as during transfer of the patient.

In the past such postoperative or pleural drainage has been effected by means of a three bottle system. This system consisted of a collection bottle, a liquid seal for gases to bubble through and prevent backflow into the patient, and vacuum regulation of suction flow.

It is desirable for the above reasons to closely monitor negative or vacuum pressures during pleural drainage. Also, if the vacuum is lost for any reason, a water seal prevents air from flowing freely back into the pleural cavity. When the patient coughs, the negative pressure can be excessive which can result in water being sucked out of the manometer into the water seal or collection chamber.

More recently, the three bottle system has been combined with a flexible and detachable blood bag in a device of the type described in U.S. Pat. No. 4,781,707. This device collected shed blood in a detachable blood bag for reinfusion to the patient. This device, however, is not suitable for cardiotomy and venous blood collection during surgery.

SUMMARY OF THE INVENTION

An improved unit is provided by this invention having combined cardiotomy and venous reservoir capabilities with filtration and defoaming for autotransfusion of cardiotomy blood and venous blood during surgery and for postoperative wound site pleural drainage of shed blood for continued autotransfusion using the same unit. Vacuum regulation in the form of a manometer combined with a water seal are integral with the unit.

The unit is comprised of a rigid, substantially cylindrical housing having a top, bottom and side walls and having an annularly disposed central substantially cylindrical filter spaced from the outer housing walls and extending from the top of the housing to a point spaced from the bottom of the unit.

The cylindrical filter is divided into an upper cardiotomy blood chamber for receipt, defoaming and filtration of cardiotomy blood and a lower venous blood chamber for receipt, defoaming and filtration of venous blood. The area between the housing side walls and the substantially cylindrical filter as well as the area between the housing side walls and an inner wall extension defines a filtered blood reservoir where filtered cardiotomy blood from the cardiotomy blood reservoir chamber and filtered venous blood from the venous blood reservoir chamber are combined.

The filtered blood reservoir has a downward slant on one side for gravity flow of blood to an outlet port for removal of blood for reinfusion.

Disposed within the filtered blood reservoir and extending along the length thereof are two long, relatively narrow chambers which extend from top to bottom of the unit and are juxtaposed relative to each other. A first chamber acts as a water seal and the second chamber acts as a manometer for postoperative use for pleural drainage and collection of shed blood for reinfusion to the patient. The two chambers are integrally formed within the filtered blood reservoir.

The cardiotomy chamber includes a support grid surrounded on both sides by an open cell sponge filter coated with a defoaming agent. The chamber also includes a pleated filter made up of a 28 micron screen filter which excludes all particles larger than 28 microns in size. The microporous screen filter is sandwiched between and supported by two layers of mesh screen.

The unit of the invention preferably uses a defoaming agent which is an antifoam silicone oil with 4.5% of silicone dioxide particles of about 4 microns in diameter suspended therein. The defoaming agent is sprayed onto the open cell sponge filter prior to emplacement within the unit. The use of a pleated filter provides a larger surface area for filtration than is provided by the nonwoven depth filters of the prior art devices resulting in more effective filtration.

The venous blood filter includes a polyurethane reticulated sponge filter having 20 pores per inch which is coated with a defoaming agent and which is supported by a grid.

The combination unit of the invention provides good throughput of both cardiotomy and venous blood by providing novel flow directors and good surface contact between blood and filters.

Several upright flow director fins surround the central venous tube inlet to direct suctioned cardiotomy blood and other additives into an inverted truncated conical member which opens into the cardiotomy reservoir chamber.

Venous entry takes place centrally at the top of the unit by means of relatively large diameter tubing to provide free flow without resistance. The venous inlet tube has an integral coiled wire reinforcement embedded therein to prevent kinking of the tubing.

The large diameter venous blood entry tubing passes through the upper cardiotomy reservoir chamber to enter the upper part of the venous reservoir chamber. The presence of the central venous tube within the cardiotomy reservoir provides for volume displacement to minimize splashing and it also serves as a flow director for incoming blood within the cardiotomy reservoir chamber. This condition helps to avoid stasis within the cardiotomy reservoir chamber.

The venous reservoir chamber is provided with an upwardly oriented substantially conical flow director to drain all venous blood toward and through the sponge filter and defoamer where the downward slant of the reservoir directs its flow by gravity to the exit or outlet port.

Another feature of this combination unit of the invention is the provision of a relatively large diameter entry port within the top of the device in communication with the cardiotomy reservoir chamber for postoperative use for pleural drainage and collection of shed blood. The provision of a top entry provides for free flow into the unit.

The invention provides an advantage of functioning as a cardiotomy reservoir and a venous reservoir for filtration and autotransfusion of cardiotomy blood and venous blood during surgery. After surgery, the same unit can be used for pleural drainage and collection of shed blood for autotransfusion to the patient. The integral water seal and manometer avoid the need for a separate manometer which is extrinsic to the unit. The use of the same unit during surgery and for pleural drainage minimizes the possibility of introducing microorganisms into the blood being transfused.

The use of the combination unit of the invention helps to conserve the blood of the patient as well as minimizing the risk of transfusion related infections and serves to return the patient's plasma and electrolytes.

BRIEF DESCRIPTION OF THE DRAWINGS

The invention will be more clearly understood by reference to the description below taken in conjunction with the accompanying drawings wherein:

FIG. 3 shows a top plan view looking down on the unit of FIG. 1.

FIG. 5 shows a sectional view as seen in the direction of lines 5—5 of FIG. 2 showing the shared vacuum line between the water seal chamber and the vacuum regulating chamber of this invention.

FIG. 6 shows a sectional view in the direction of lines 6—6 of FIG. 2.

FIG. 7 shows a sectional view of the water seal as seen in the direction of lines 7—7 of FIG. 3.

DESCRIPTION OF THE PREFERRED EMBODIMENTS

Figure 1:
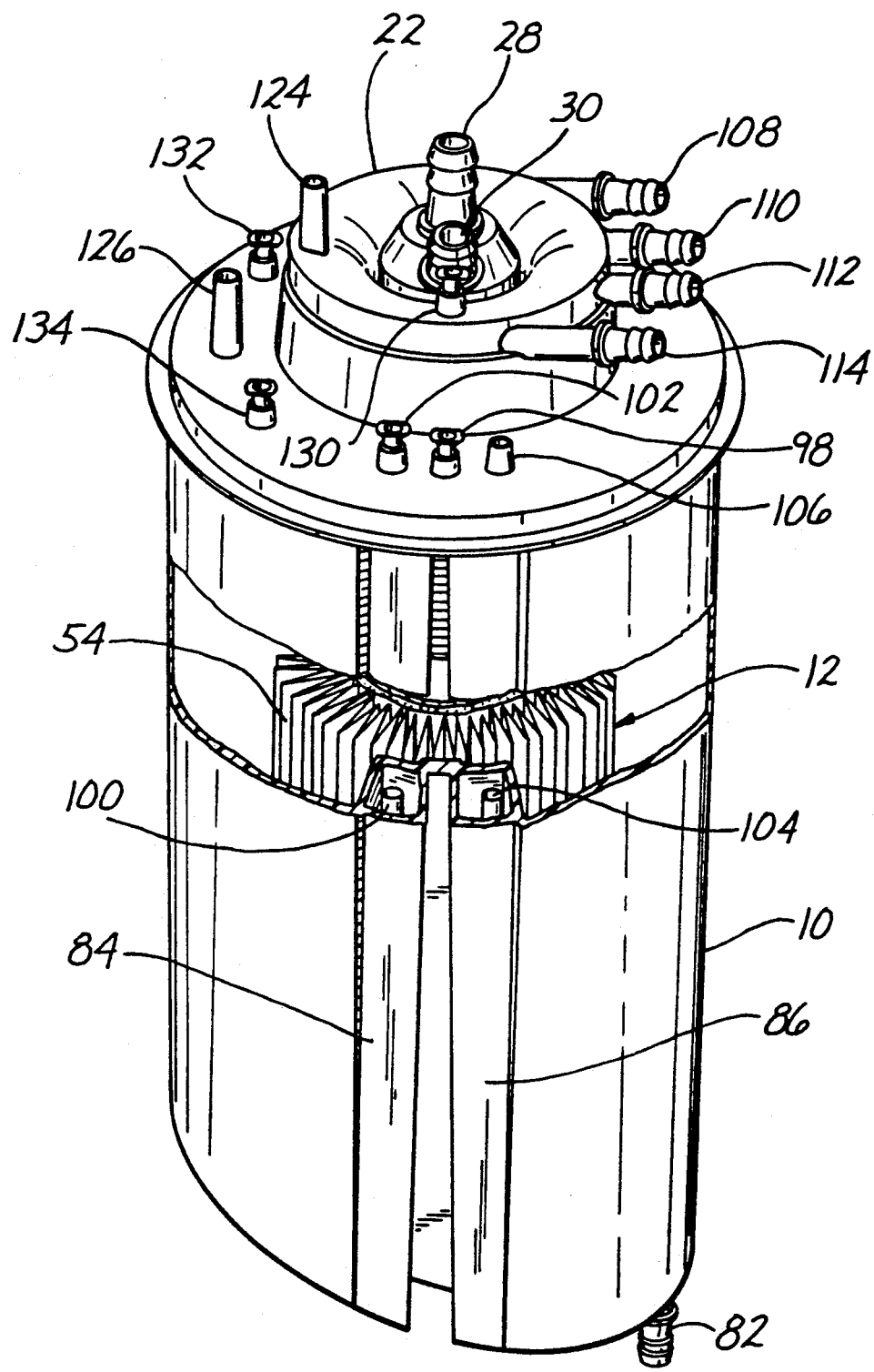
FIG. 1 shows a perspective view of the unit of this invention.

Referring now to FIG. 1, a perspective view of the cardiotomy/venous reservoir/pleural drainage unit can be seen. The unit is comprised of a rigid, substantially cylindrical housing in the form of a walled canister 10. Disposed within the canister or housing 10 is an axially disposed substantially cylindrical filter 12 which is spaced from the outer housing walls and extends from the top of the housing to a point spaced from the bottom of the unit. As shown in greater detail in FIG. 4, the canister or housing 10 includes outer walls 14. The area between the outer walls 14 and the filter 12 defines a filtered blood collection reservoir 16.

The walled canister 10 is formed by the outer walls 14 disposed between a base 18 and a top or a lid 20 that is sometimes referred to as a cap. Preferably, the canister 10 is formed of a clear plastic material.

Figure 4:
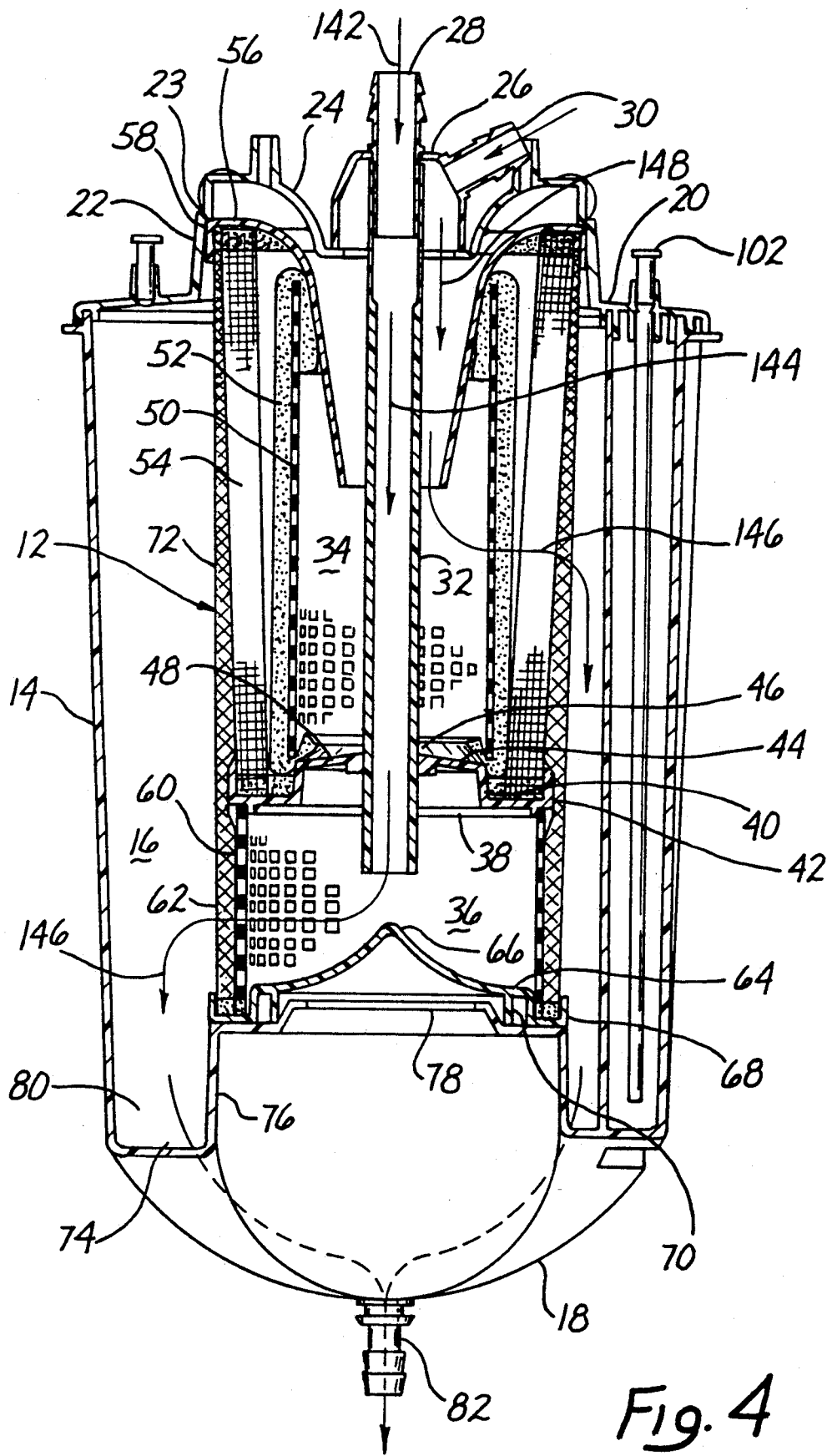
FIG. 4 shows a sectional view of the unit taken in the direction of lines 4—4 of FIG. 3.

The cap 20 is seated and sealed on the walls 14 of the canister in a tongue and groove manner as can be seen in the sectional view of FIG. 4. The cap 20 has an upstanding circular boss 22 having a shoulder 23 within its sidewalls and has sloping walls 24 that slope downwardly to a centrally disposed knob 26.

The knob 26 is provided with a central entry port 28 for the introduction of venous blood and a side entry port 30 for the introduction of fluids during pleural drainage. Each of the ports 28 and 30 are fitted with exterior barbs for the connection of tubular members thereover.

The venous entry port 28 is disposed axially with respect to the canister 10. It is connected to an elongated tubular member 32 which extends into the cylindrical filter 12.

The filter 12 is divided into an upper cardiotomy reservoir chamber 34 and a lower venous reservoir chamber 36.

The cardiotomy chamber 34 is separated from the venous reservoir chamber 36 by means of a circular member or disc 38 upon which is disposed a circular member 40. Circular member 40 contains an outer channel 42 for reception of filter material and has a substantially centrally disposed boss 44 with a central passage 46 for passage of the elongated tube 32 therethrough. The boss 44 on circular member 40 has a slightly sloping surface 48 for purposes of directing cardiotomy blood towards the walls of the filter 12.

The elongated tubular member 32 is sealed with respect to the passage 46 through boss 44. This permits venous blood to pass downwardly through the cardiotomy chamber 34 without contact therewith. The elongated member 32 then discharges venus blood into the upper portion of venous reservoir chamber 36.

The cardiotomy reservoir chamber 34 includes a support grid 50 which provides support for a polyurethane sponge foam 52. As can be seen in FIG. 4, the polyurethane foam is wrapped around the bottom and top areas of the grid 50. The polyurethane foam 52 is coated with a defoaming agent which is preferably an antifoam silicon oil with approximately 4.5 of silicon dioxide particles of about 4 microns in diameter suspended therein. The defoaming agent is sprayed onto the polyurethane open cell sponge filter prior to implacement within the canister 10. Preferably the sponge filter has a pore count of 80 pores/inch.

Surrounding the open cell polyurethane foam 52 is a pleated filter 54. The pleated filter includes a relatively small mesh support material which is pleated as a single unit with a microporous woven screen filter of microns. Preferably this filter is a 28 micron filter.

The bottom of the pleated filter 54 is cemented to the circular member 40 and the top of the pleated filter is cemented to flow director 56. Thus, the pleated filter 54 effectively seals the cardiotomy chamber from venous reservoir chamber 36 and filtered blood collection reservoir 16.

The flow director 56 is in the form of a truncated funnel having rounded sloping walls at the mouth thereof and a downturned flange 58 by which the flow director 56 is secured or cemented to boss 22 on cap or lid 20.

The pleated filter 54 can be formed from a ribbed polypropylene mesh and woven polyester screen. The pleated filter formation allows for extensive movement of fluid therethrough, while at the same time allowing a greater surface area for filtration than a mere cylindrical filtration member. Thus, the pleated filter serves to provide a greater throughput with less back pressure because of the broadened filtration surface area.

In the venous reservoir chamber 36 there is a large mesh grid 60 which acts as a support backing for polyurethane open cell sponge filter 62. The open cell sponge filter 62 is coated with a defoaming agent similar to that of filter 52 in the cardiotomy chamber 34 and provides minimal filtering to the venous blood. Preferably, the sponge filter 62 has a pore count of 20 pores per inch.

Open mesh grid member 60 of venous reservoir 36 is secured at the upper end to circular disk member 38 at the base of cardiotomy chamber 34. The lower end of the mesh grid 60 is secured to a circular flow directing member 64. Circular member 64 projects upwardly into a peak 66 and is provided with a peripheral channel member 68 which extends around circular member 64. A downwardly oriented flange 70 on member 64 which also extends around the outer area of member 64 provides strength to member 64.

The lower end of open mesh grid 60 of venous reservoir 36 is secured within channel 68 of circular member 64. Also, the open mesh sponge material 62 supported by grid 60 and extends around carditomy chamber 34 and venous chamber 36 is secured to flow director 56 and is secured at its base within channel 68 of member 64.

The filters described herein are secured to the respective members by means of a cement or plastic material which does not permit the passage of fluid therethrough. In this manner, the respective cardiotomy chamber 34 and venous chamber 36 are sealed with respect to each other and with respect to the outer filtered blood collection chamber 16 so that any blood or fluid entering the cardiotomy chamber 34 or venous chamber 36 must pass through the respective filters in order to exit these chambers.

The peaked area 66 of circular flow directing member 64 acts to direct the flow of blood contacting the circular member 64 outwardly to the filter area of venous reservoir chamber 36.

The outer walls 14 of the canister 10 extend downwardly to a point below the venous reservoir 36 and extend inwardly at 74 and upwardly at 76 and are secured to disk member 78 which underlies flow director 64 of venous reservoir chamber 36.

The crosswise extension 74 and upward extension 76 together with facing wall 14 forms a deep trough or channel 80. The trough 80 forms the base 18 of the canister 10 and slopes downwardly toward outlet port 82 for the exit of blood and fluid passing through cardiotomy chamber 34 and/or venous chamber 36. In this manner all blood and fluid is drained by gravity through channel 80 toward the port 82.

Figure 2:
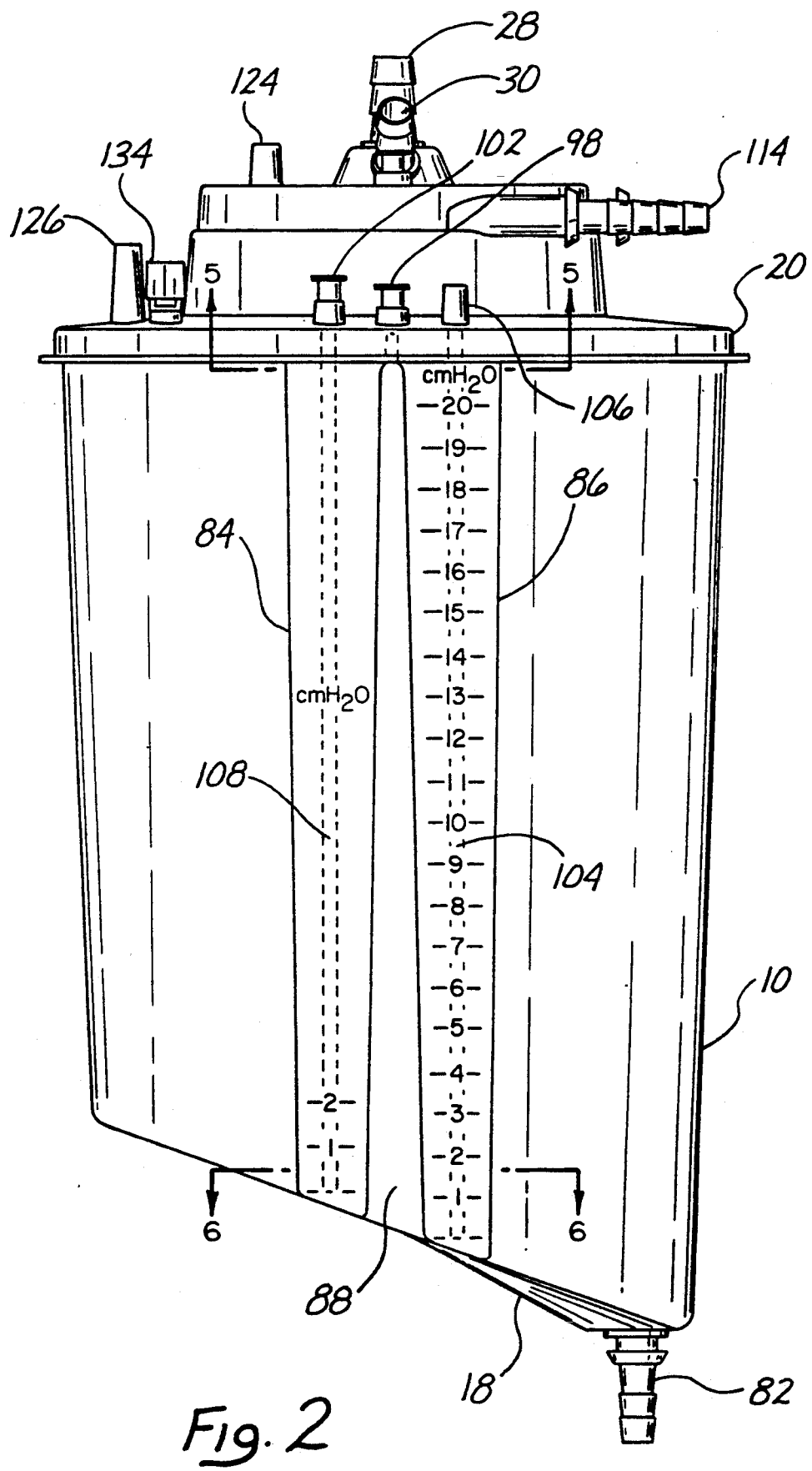
FIG. 2 shows a side elevation view of the unit of substantially the same frontal portion as seen in FIG. 1.

Disposed within the outer wall 14 and extending the length of the canister 10 is a water seal chamber 84 and a manometer 86. As shown in FIGS. 1, 2, 4, 5, 6 and 7 the respective chambers 84 and 86 are each formed as an elongated chamber extending between the cap member or lid 20 and the base 18. The water seal 84 and the manometer 86 are integrally formed yet completely separate from the cardiotomy chamber 34, venous reservoir chamber 36, and filtered blood chamber 16. As shown in FIG. 6, the chambers 84 and 86 are substantially the same being formed of a oblong cross section divided by a spacer wall or tongue 88. Spacer wall 88 as shown in FIG. 2 tapers slightly as it rises from the base 18 to the cap 20.

As shown in FIG. 7, the cap or top 20 of the canister 10 is secured to the side walls 14 of the unit by means of a tongue and groove or flange orientation. The portion of the cap or lid 20 which overlies the water seal chamber 84 and manometer 86 is sealed with respect to the remainder of the cap and interior areas of the canister or unit 10. This can be seen especially in FIG. 5.

As shown in FIG. 5 a flanged area 90 extends perpendicularly from the inner portion of the cap 20 and is spaced from a similarly shaped flanged area 92. The trough 94 formed between the flange 90 and the flange 92 receives the upper portion of water seal chamber 84, spacer 88 and manometer 86 in a tongue and groove manner as partially shown in FIG. 7. In this manner, the water seal chamber 84 and manometer 86 are completely sealed with respect to the other chambers within the unit 10.

Within the inner flange 92 is a crosswise flange 96 perpendicular to cap 20 which divides the area circumscribed by flange 92 into two parts.

When in place, the upper portion of the manometer 86 and water seal 84 fits within the groove 94 such that they are completely sealed from one another except for port 98 which is bifurcated by flange 96. Port 98 is for the connection of a vacuum. The bifurcation of the port 98 by means of flange 96 divides the vacuum suction pressure into half within the water seal chamber 84 and half within the manometer chamber 86 in the manner of a baffle.

The showing of the water seal chamber 84 of FIG. 2 includes a dotted showing of an elongated tube 100 therein which extends from and is connected to port 102 and extends downwardly to a point just short of the bottom of the water seal chamber 84.

Similarly, an elongated tube 104 shown in dotted configuration within the manometer 86 of FIG. 2 extends from and is connected to vent port 106 and extends downwardly point just short to a of the bottom of manometer 86.

The water seal chamber 84 and manometer 86 have water therein and are utilized for regulation of a vacuum applied to port 98 during pleural drainage. Normally the water seal chamber 84 has water to approximately 2 cm in height and manometer chamber 86 has water to approximately 20 cm in height. The function of the water seal chamber 84 and manometer 86 are subsequently described.

Looking more particularly at the cap or lid 20 of the canister 10 as shown in FIGS. 1, 2, 3 and 4, there can be seen a number of fittings attached thereto. Four of these fittings can be seen in the form of barbed tubular inlet ports 108, 110, 112, and 114. The inlet ports 108 through 114 can be utilized for cardiotomy suctioning when the unit serves the function of a cardiotomy reservoir during surgery. The cardiotomy suction ports 108 through 114 can also be used for the introduction of fluids such as additional saline or banked blood into the unit if desired. The cardiotomy suction ports are generally sealed with caps over their openings when not in use. They are also sealed during the time the unit is being used for pleural drainage as explained hereinafter.

Within the cap 20 and more particularly within the boss 22 are disposed curved upright perpendicular flanges 116, 118, 120, 122, and 123. These flanges 116–123 entirely fill the space between the outer portion of boss 22 and flow director 56. The flanges 116–123 are shown in dotted lines in FIG. 3.

The function of the flanges 116–123 is to effectively direct and channel incoming cardiotomy blood suctioned through ports 108, 110, 112, and 114 down through flow director 56 for filtration within cardiotomy chamber 34.

The cap 20 can be further seen to have a port 124 which is a quick prime port which opens into boss 22 for communication with the cardiotomy chamber 34. Fluid can be introduced into the interior of the cardiotomy reservoir chamber 34 by means of the quick prime port 124 to initiate the start up of the cardiotomy suction or other functions. Flow through port 124 is not absolutely necessary but it is utilized in a quick priming manner by most surgical teams.

In order to help the unit displace air within it, a vent port 126 is provided. The vent port 126 can be opened to allow for venting of air, depending upon the particular functions that are being undertaken during the surgical procedure.

Because of the venous component of the reservoir, wall suction cannot be used during surgery. Roller pumps are utilized in order to provide negative pressure to the canister 10. The roller pumps, not shown, are utilized in conjunction with the tubing connected to cardiotomy ports 108, 110, 112, and 114.

Drug administration ports 128 and 130 are disposed opposite each other within the boss 22. They are preferably provided with luer lock connections so that a syringe or other male luer fitting can be connected thereto. These administration ports allow for the introduction of drugs within the filter prior to the blood or other fluid passing therethrough.

The cap 20 is also provided with drug administration ports overlying the filtered blood chamber 16 between the filter 12 and the outer walls 14.

These drug administration ports are shown by numerals 132 and 134 along the outer area of the cap 20. The ports 132 and 134 are also provided with luer lock fittings so that a syringe or other male luer fitting can be connected thereto. These luer lock drug administration ports allow for drug administration to blood having already passed through filter 12.

Port 134 also functions as a water seal connector as hereinafter described when the unit is being used for pleural drainage.

The top 20 or cap is provided with valves to provide for release of positive and negative pressure. This is in part provided by a combination high negative/low positive pressure relief valve 160 in the form of an umbrella valve. A low negative pressure relief valve 162 is also provided. These respective valves allow for the bleeding and sustaining of pressure within the unit 10 so that it will neither collapse nor expand inordinately. At the same time, the valves have been set for the operating conditions necessary for both cardiotomy reservoir and venous reservoir usage, as well as pleural drainage usage. It is known to set these valves so that they can maintain the negative pressure of approximately minus twenty centimeters of water post-operatively for pleural drainage.

Figure 8:
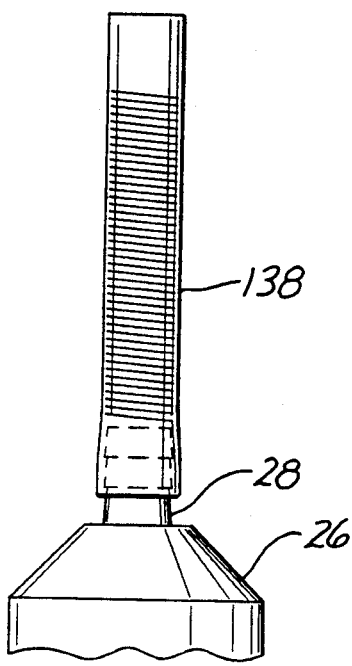
FIG. 8 shows a partially broken away view of the top venous entry port with attached non-kinking tubing.
Figure 9:
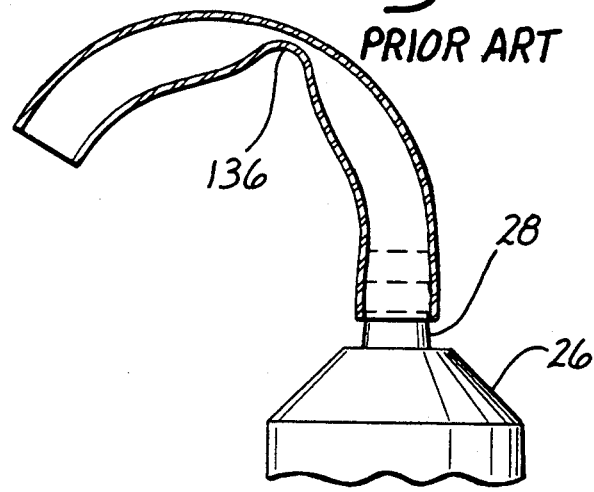
FIG. 9 shows a prior art showing of a tube which is subject to kinking and therefore can block the inflow.
Figure 10:
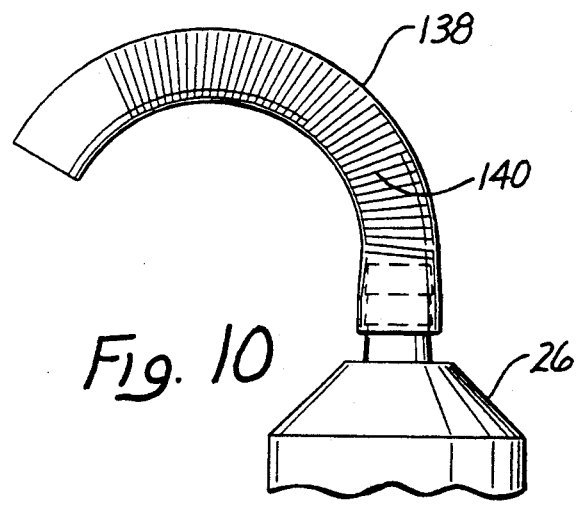
FIG. 10 shows an improved reinforced tubing in a bent configuration which resists and avoids kinking during use.
Figure 11:
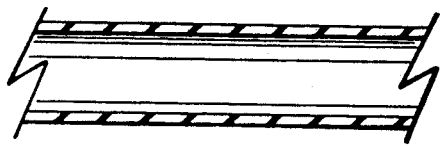
FIG. 11 shows a partial section of a prior art tubing.
Figure 13:
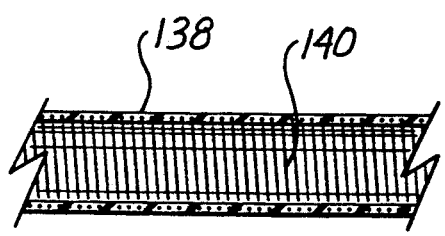
FIG. 13 shows a partial section of the improved tubing of the invention shown in FIG. 10.

The barbed inlet port 28 for the introduction of venous blood is preferably utilized with a non-kinking tubular member 138 as shown in FIGS. 8 and 10 and 13. This non-kinking tube 138 as shown in FIG. 13 has a spiral reinforcement of wire embedded therein for several inches. The spiral reinforcement is shown at 140 in FIGS. 8, 10 and 13. This tubing should be contrasted with the prior art tubing as shown in FIGS. 9 and 11 which are subject to kinking, as shown in FIG. 9 at 136. It is evident that the kinking at point 136 of FIG. 9 could easily cause the restriction of flow into the cardiotomy/venous reservoir unit.

In operation, when the cardiotomy reservoir/venous reservoir unit 10 is being used during surgery, lines 108, 110, 112 and 114 are used for cardiotomy suctioning of fluid surrounding the operative site. At the same time, venous blood is drained from the patient by means of a connection through a venous cannula inserted into the right atrium. The venous drainage from the patient is introduced into the invention unit 10 through inlet port 28 where it is passed through elongated tubing 32 directly into venous reservoir chamber 36.

The direction of flow can be seen by following the path of arrow 142, 144 and 146 showing passage of the venous blood from the inlet port 28 through the tube 32 into the venous chamber 36 and through the support mesh 60 and defoaming sponge 62 into the chamber 16.

At the same time, blood and fluid suctioned by cardiotomy suckers into inlet ports 108, 110, 112 and 114 enter the space between the boss 22 and the flow director 56 and at the same time are channeled by means of the upright perpendicular flanges 116, 118, 120, 122 and 123 to be drawn downwardly in the direction of arrow 148 within flow director 56 into cardiotomy chamber 34. Here, the blood is partially directed by means of the external walls of tube 32 into contact with support grid 50, sponge defoamers 52, pleated filter 54, and sponge defoamer 72 for passage into fitted blood chamber 16 in the manner indicated by arrow 150.

The blood exiting the filter 12 from the cardiotomy chamber 34 and from the venous chamber 36 are combined within filtered blood chamber 16. The blood in chamber 16 flows by gravity toward outlet port 82.

From outlet port 82 the blood is passed to a blood oxygenator, not shown, and returned to the patient directly through an aortic annula. In this manner, the cardiotomy blood, as well as the venous blood can be returned to the patient. Thus, there is autotransfusion of the cardiotomy blood as well as the venous blood from the patient.

It has been found to be particularly advantageous to have venous entry through the top of the unit 10 as compared with the bottom entry of prior art venous reservoir units. The top entry eliminates the possibility of blood stagnation with consequent clot formation and resistance to inflow into the venous reservoir caused by back pressure of stagnant blood. A further advantage consists of the use of a preferably one half inch diameter flexible tubing connection 138 described above. The venous reservoir compartment 36 of the invention unit can accommodate flow rates of up to seven liters per minute.

The filtration of the cardiotomy blood within the cardiotomy reservoir 34 provides filtration through a 28 micron pleated filter which permits flow rates of up to four liters per minute. A preferred capacity of 390 ml. reduces the chances of occlusion of the filter.

During intraoperative use, it is important that the high negative/low positive pressure relief valve 162 remain unoccluded, since pressurization of the unit 10 can force air emboli back through an attached arterial filter line to the patient.

The pleural drainage port 30 is capped during intraoperative procedures as is the low negative pressure relief valve 160 for proper function of the high negative/low positive pressure relief valve 162. The vacuum vent port 126 must be open during intraoperative procedures in order to prevent pressurizing of the unit 10.

Normally, the cardiotomy reservoir filter sponge 54 and defoamer 52 are wetted prior to use in order to minimize blood breakthrough volume. This can be accomplished by introducing a priming solution through either the quick prime port 124 or one of the drug inlet ports 128 or 130. Negative pressure suctioning throughout the unit 10 is preferably achieved by means of a roller pump, not shown, which is used in conjunction with tubing connected to cardiotomy inlet ports 108, 110, 112 and 114. The drug inlet port 132 and the drug inlet port 134 which is also used for a water seal communication connection, are kept capped during intraoperative use.

The postoperative use of the combination unit 10 of the invention is as a pleural drainage device. The postoperative setup can be seen in FIG. 12. The cardiotomy suctioning tubing should be removed from inlet ports 108, 110, 112 and 114 and capped off. The venous inlet port 28 should also be capped off.

Figure 12:
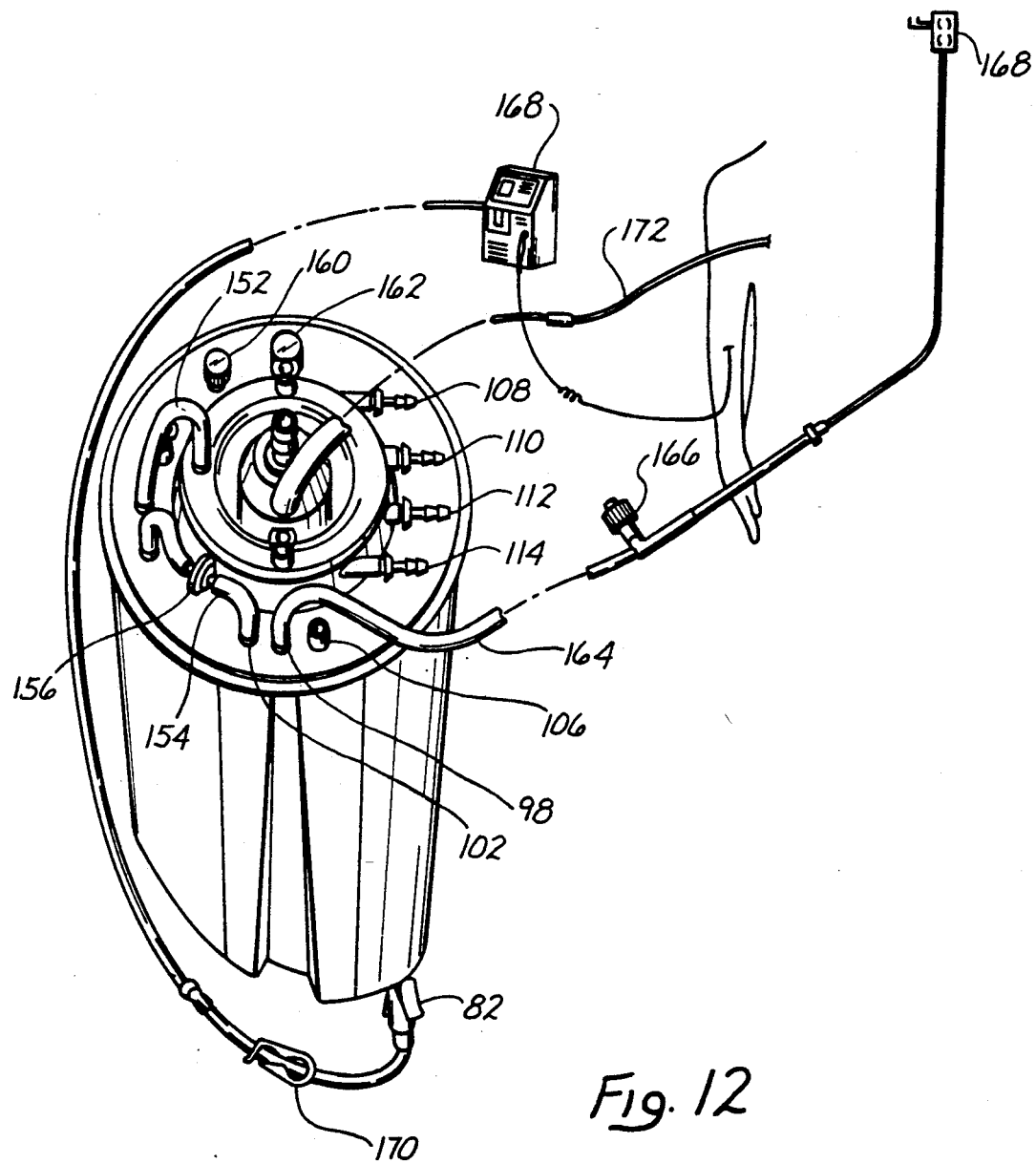
FIG. 12 illustrates the setup utilized for postoperative pleural drainage of shed blood.

A shunt line 152 as shown in FIG. 12 should be connected between the quick prime port 124 and the vent vacuum port 126. The low negative pressure release valve 162 is uncapped and preferably attached to a micro-air filter, not shown. Any intraoperative lines connected to the luer connectors such as 128, 130 and 132 are removed and capped. The caps are removed from the water seal port 102 and the vacuum port 98. The water seal chamber 84 is filled through port 102 to the desired level. The water manometer 86 is filled through the water manometer vent port 106 which is kept open at all times. A syringe can be used for the purpose of filling the water seal chamber 84 or the manometer 86.

A reservoir/water seal communication line 154 and containing a duck billed valve 156 is connected between the port 134 and the water seal port 102. The pleural drain lines 172 from the patient to the pleural drainage inlet port 130 are connected. The combination cardiotomy reservoir/venous reservoir/pleural drainage unit 10 is positioned below the level of the drainage from the patient. A line 164 as shown in FIG. 12 having an adjustable flow regulator 166 in the turned off position is connected to a vacuum source 168 and to the vacuum inlet port 98. The vacuum is turned on to a setting between 30 centimeters water and 200 centimeters water. The integrated water manometer 86 will then regulate the vacuum to the prescribed vacuum level. When fifty millimeters of shed blood have been collected within the reservoir 16, it can be reinfused to the patient using an infusion pump 168 connected to the outlet port 82 through the tube clamp 170. Collection followed by reinfusion can then be followed in any preferred manner.

The function of the shunt line 152 is to transfer blood from the interior of the boss 22 directly into the outer chamber 16 bypassing the filter 12. This situation would happen in the eventuality there were excessive bleeding such that the cardiotomy chamber 34 within boss 22 were filled more rapidly than could be filtered through the cardiotomy reservoir chamber 34. This might also be necessary in the eventuality that the filter 12 were occluded in some fashion. This would still allow the introduction of blood without interference. In this instance, the blood would need to be filtered prior to patient infusion.

The function of the water seal communication line 154 with the duck billed valve 156 and an elastomeric one way flap 158, not shown, assures that the vacuum is drawn toward the water seal chamber 84 and the manometer chamber 86. At the same time, there is no possibility of air being drawn in the opposite direction, which is prevented by the one way duck billed valve 156 and one way flap 158. If it is necessary to disconnect the vacuum from port 98, the water seal chamber 84 and line 154 with valve 156 and flap 158 prevent the introduction of air. This is useful if the patient must be moved.

Normally, the unit is used for pleural drainage after use of the unit for cardiotomy blood filtration and venous blood filtration with autotransfusion. In the eventuality that the unit is used solely as a pleural drainage unit, the quick prime port 124 or other port can be used to prime the filter 12 to reduce the amount of blood necessary for wetting of the filter 12.

As shown in FIG. 5 as previously explained, a flange 96 acts as a baffle to divide the space within cap 20 between the water seal chamber 84 and the manometer chamber 86. The vacuum hookup port 98 is shown with the baffle or flange 96 bisecting the opening. As a consequence, vacuum provided through the port 98 is allowed to enter both the water seal chamber 84 and the manometer chamber 86 and draw down on both chambers to create the regulating function through the atmospheric port 106.

Any suitable type of baffle or flange 96 can be arranged between the two respective chambers 84 and 86. The one requirement is that a vacuum must be established, with the appropriate water seal 84 and a vent, such as vent 106 to provide the regulated twenty centimeters of water vacuum.

In order to provide pleural drainage from the pleural-medastinal of a patient, it is necessary to provide a low negative pressure. When the unit 10 is to be used as a pleural drainage/autotransfusion unit, it draws liquid and air from a patient's pleural or chest cavity area, thereby creating that negative pressure. The pressure is established by means of the vacuum being drawn on through vacuum inlet port 98 which communicates with chamber 16 through the water seal communication line 154. This in turn creates a negative pressure through cardiotomy reservoir 34 upwardly through the top of the unit through pleural drainage inlet port 30.

The pressure of the vacuum at vacuum port 98 provided by a hospital vacuum line is in excess of twenty centimeters of water. This causes the water column to be pulled down through tube 104 within manometer 86 which is in communication with atmospheric vent port 106 which allows air to be drawn in. The column of fluid in tube 104 regulates the negative pressure obtained in the patient's chest cavity. As the fluid is pulled down, it causes a bubbling at the base of the tube 104 within manometer chamber 86. The bubbling continues inasmuch as the atmospheric vent 106 allows for continued pull therethrough, while at the same time maintaining a vacuum of up to twenty centimeters of water, depending on the column of water within the manometer tube 86.

The vacuum being drawn through the water seal communication line 154 from port 134 within the interior of the entire chamber allows for a constant negative pressure pull through port 30 of up to thirty centimeters of water. This is due to the fact that the vacuum provided within the water seal chamber 84 is transmitted from port 102 through port 134 to the interior of the unit 10 as mentioned above. This maintains and controls the negative pressure through port 30.

In order to preclude entry of atmospheric air within unit 10 and allow for a continuous vacuum, water seal chamber 84 provides a water seal. The water seal allows for the vacuum drawn through port 102 down through tube 100 to be maintained with approximately two centimeters of water overlying tube 100.

Fluid drawn from the patient's pleural area, flows into pleural drainage inlet port 30 and down through the flow director 56. The fluid then flows into cardiotomy reservoir chamber 34 and through theddfoamer sponge 52 and filter 54 as described above. The flow is allowed to collect in chamber 16 where it flows directly and downwardly to outlet 82. The fluid from outlet 82 can then be pumped by a volumetric infusion pump back to the patient through an intravenous connection as explained above.

The water seal also permits the movement of the patient and prevents the introduction of air emboli when the vacuum is disconnected.

The cardiotomy reservoir/venous reservoir/pleural drainage unit with integral water seal and manometer described above provides an improved unit. First, the unit can be used for combined cardiotomy and venous reservoir filtration and reinfusion to the patient for autotransfusion of cardiotomy blood and venous blood during surgery. After surgery, the same unit can be used for postoperative wound site pleural drainage of shed blood for continued autotransfusion using the same unit. The vacuum regulation in the form of a manometer combined with the water seal is integral with the unit and does not require additional vacuum regulation.

Preferably, the unit is comprised of a clear plastic material so that the contents of the unit can be readily seen.

The provision of various flow director means, including the flow director 56 and the perpendicular fins 116, 118, 120, 122 and 123 disposed within boss 22 predisposes to efficient filtering combined with the provision of a pleated filter as described herein.

A separate venous reservoir having a top entry avoids back pressure and the formation of blood clots while at the same time provides minimal filtration and defoaming so that the venous blood is minimally degraded by the process.

A particular cost advantage is provided since the unit can be used for a cardiotomy reservoir, a venous reservoir, and postoperatively as a pleural drainage unit. Prior to the current device, each of these reservoirs had to be used singularly with an increased risk of the introduction of bacteria during the connection and disconnection of various lines. Also, the provision of separate devices requires more wetting of the filter material and an increased cost for the necessity of purchasing a separate unit for each function.

Based upon the foregoing advances of the art as specified herein, it is believed that this invention should be entitled to broad consideration and substantial breadth and scope applied to the following claims.

Various modifications of the invention are contemplated and can be resorted to by those skilled in the art without departing from the spirit and scope of the invention as defined by the following claims.

We claim:

1. A combination cardiotomy reservoir, venous reservoir, and pleural drainage unit having a vacuum regulating system therein for autotransfusion comprising:
    a single vessel having a top, a bottom, and sidewalls formed of a material which resists collapse under the application interiorly of a vacuum under the conditions of use;
    said vessel being divided interiorly into a plurality of chambers, at least one chamber being adapted for use as a cardiotomy reservoir, at least one chamber being adapted for use as a venous reservoir, and at least one chamber which is separate from said cardiotomy and venous reservoir chambers being adapted for use as a vacuum regulating system;
    a plurality of ports within said vessel for the introduction and withdrawal of fluids including at least one inlet port for blood and body fluids which is in communication with said cardiotomy reservoir chamber, at least one inlet port for blood and body fluids which is in communication with said venous reservoir chamber, at least one outlet port for blood which is in communication with said cardiotomy reservoir chamber and said venous reservoir chamber, and at least one port in communication with said vacuum regulating system for the application of a vacuum; and,
    filtration means for body fluids disposed within said vessel between said at least one inlet port for blood and body fluids for said cardiotomy reservoir chamber and said at least one outlet port for blood so that body fluids entering said cardiotomy reservoir chamber must pass through said filtration means before exiting through said at least one outlet port for blood.

2. A unit as claimed in claim 1 wherein said vacuum regulating chamber includes a liquid seal and a balanced column of liquid to provide a specific control vacuum to the unit upon the application of a vacuum to said at least one port in communication with said vacuum regulating system.

3. A unit as claimed in claim 2 wherein said cardiotomy reservoir chamber and said venous reservoir chamber are provided with a foam blood defoamer for body fluids which is in fluid connection with said at least one outlet port for blood; and,
    filtration means for body fluids disposed within said vessel between said at least one inlet port for said venous reservoir chamber and said at least one outlet port for blood so that body fluids entering said venous reservoir chamber must pass through said filtration means before exiting through said at least one outlet port for blood.

4. The unit as claimed in claim 3 wherein said foam blood defoamer includes a support grid for said foam defoamer and said filtration means in communication with said cardiotomy reservoir includes a pleated filter.

5. A combination cardiotomy reservoir, venous reservoir, pleural drainage reservoir for autotransfusion containing an integral vacuum regulation system comprising a non-collapsible top and bottom joined by non-collapsible sidewalls, said unit being structured and arranged so that said unit includes at least one cardiotomy reservoir chamber which receives cardiotomy blood directly within the walls, at least one venous reservoir chamber which receives body fluids directly within its walls and at least one reservoir separate from said cardiotomy and venous reservoir chambers for use as a vacuum regulating system comprising:
    a plurality of ports within said unit including at least one inlet port connected to said cardiotomy reservoir to which a tube can be connected for receipt of draining fluids from the body of a patient or for receipt of fluids for cardiotomy functions;
    at least one inlet port to which a tube can be connected for receipt of venous blood from the body of a patient;
    at least one outlet port connected to said unit which is in communication with said cardiotomy reservoir and said venous reservoir for connection to a pump for the withdrawal of fluids from said unit and delivery back to a patient in order to provide autotransfusion, or to a drain;
    a vacuum regulating system enclosed within said non-collapsible unit and occupying said at least one reservoir for use as a vacuum regulating system and including a vacuum regulating chamber and a liquid seal chamber;
    at least one inlet port in communication with said liquid seal chamber and said vacuum regulating chamber for connection to a vacuum whereby said liquid seal chamber and said vacuum regulating chamber can be filled with liquid to a given level and, upon application of a vacuum, provide a controlled vacuum within said unit for removal of body fluids from a patient under a controlled vacuum; and, filtration means interposed between said inlet to said cardiotomy reservoir and said outlet from said unit and filtration means interposed between said inlet for said venous reservoir and said outlet from said unit for filtration of body fluids received within said cardiotomy chamber and said venous reservoir chamber.

6. The unit as claimed in claim 5 wherein said venous reservoir has a top and a bottom and wherein said at least one inlet port for said venous reservoir is in communication with the top of said venous reservoir chamber.

7. The unit as claimed in claim 5 wherein said cardiotomy reservoir chamber has a top and a bottom and sidewalls and wherein there further comprises flow directing means disposed between said inlet to said cardiotomy reservoir chamber and the top of said cardiotomy reservoir chamber so that blood entering said cardiotomy reservoir chamber is directed to the walls of said cardiotomy chamber.

8. The unit as claimed in claim 5 wherein said cardiotomy reservoir chamber overlies and is contiguous with said venous reservoir chamber, and said cardiotomy reservoir chamber and said venous reservoir chamber are disposed axially within said unit.

9. The unit as claimed in claim 8 wherein said cardiotomy respective filtration means, so that the respective sidewalls of said cardiotomy chamber and the sidewalls of said venous chamber are formed by said filtration means to form a hollow receptacle into which body fluid from said respective inlet ports are introduced.

10. The unit as claimed in claim 9 further comprising foam blood defoaming means supported by a support means which is in fluid communication with said cardiotomy reservoir and with said venous reservoir chamber so that body fluids passing through the respective chambers also pass through said defoaming means.

11. The unit as claimed in claim 9 further comprising flow direction means disposed within said venous reservoir chamber to direct blood entering said chamber to the walls of said chamber.

12. The unit as claimed in claim 5 further comprising a separate inlet port into said cardiotomy reservoir for cardiotomy functions and a second separate inlet port into said cardiotomy reservoir for pleural drainage usage.

13. A combination cardiotomy reservoir, venous reservoir, pleural drainage reservoir for autotransfusion containing an integral vacuum regulation system comprising a non-collapsible top and bottom joined by non-collapsible sidewalls, said unit being structured and arranged so that said unit includes at least one cardiotomy reservoir chamber which receives cardiotomy blood directly within the walls, at least one venous reservoir chamber which receives body fluids directly within its walls and at least one reservoir separate from said cardiotomy and venous reservoir chambers for use as a vacuum regulating system comprising:

a plurality of ports within said unit including at least one inlet port connected to said cardiotomy reservoir to which a tube can be connected for receipt of draining fluids from the body of a patient or for receipt of fluids for cardiotomy functions;

at least one inlet port to which a tube can be connected for receipt of venous blood from the body of a patient;

at least one outlet port connected to said unit which is in communication with said cardiotomy reservoir and said venous reservoir for connection to a pump for the withdrawal of fluids from said unit and delivery back to a patient in order to provide autotransfusion, or to a drain;

a vacuum regulating system enclosed within said non-collapsible unit and occupying said at least one reservoir for use as a vacuum regulating system and including a vacuum regulating chamber and a liquid seal chamber;

an elongated conduit within said liquid seal chamber;

connection means connected to said elongated conduit;

a through port with connection means in communication with said cardiotomy reservoir chamber adapted for connection to said connection means on said elongated conduit within said liquid seal chamber;

connection means in communication with said liquid seal chamber and said vacuum regulation chamber for applying a vacuum thereto;

at least one inlet port in communication with said liquid seal chamber and said vacuum regulating chamber for connection to a vacuum whereby said liquid seal chamber and said vacuum regulating chamber can be filled with liquid to a given level and, upon application of a vacuum, provide a controlled vacuum within said unit for removal of body fluids from a patient under a controlled vacuum; and, filtration means interposed between said inlet to said cardiotomy reservoir and said outlet from said unit and filtration means interposed between said inlet for said venous reservoir and said outlet from said unit for filtration of body fluids received within said cardiotomy chamber and said venous reservoir chamber.

14. The unit as claimed in claim 13 further comprising;

a baffle between said vacuum regulating chamber and said liquid seal chamber having an opening to allow a vacuum to be applied simultaneously to said vacuum regulating chamber and said liquid seal chamber.

15. A combination cardiotomy reservoir, venous reservoir, and body drainage autotransfusion unit with a vacuum regulating system integrally formed therein comprising:

a non-collapsible canister having an outershell with a cardiotomy reservoir, a venous reservoir, and a vacuum regulating system disposed separately therein;

a bottom portion to said outer shell;

a cap overlying said outershell;

at least one inlet port means for introducing body fluid into said cardiotomy reservoir to provide for pleural drainage and to provide cardiotomy functions for autotransfusion;

at least one inlet port means for introducing venous blood into said venous blood reservoir to provide for autotransfusion of venous blood;

at least one outlet port means disposed within the bottom of said reservoir in communication with said cardiotomy reservoir and with said venous blood reservoir for the removal of fluids from said canister;

filtration means interposed within said cardiotomy reservoir between said at least one inlet port means for said cardiotomy reservoir and said outlet port means for said body fluid;

foam defoaming means interposed within said cardiotomy reservoir between said at least one inlet port means and said outlet port means for said body fluid;

an elongated vacuum regulating chamber within said canister in adjacent relationship to said cardiotomy reservoir and said venous reservoir but separated therefrom by a wall from the internal portions of said canister;

a conduit within said elongated vacuum regulating chamber extending toward the bottom of said chamber having an atmospheric vent connected thereto;

a vacuum connection to said elongated vacuum regulating chamber;

means for connecting said elongated vacuum regulating chamber with the interior of said canister to maintain a vacuum in said canister during body fluid drainage, said vacuum being equivalent to a column of liquid within the elongated chamber; and, liquid seal chamber within said canister in adjacent relationship to said cardiotomy reservoir chamber and separated from said vacuum regulating chamber and from the interior of said canister by a wall and which interconnects said vacuum regulating chamber with said canister interior.

16. The combination autotransfusion unit as claimed in claim 15 further comprising flow directing means in communication with said at least one inlet port means for introducing body fluid into said cardiotomy reservoir and which is in fluid communication with said cardiotomy reservoir for direction of flow into said cardiotomy reservoir.

17. The combination autotransfusion unit as claimed in claim 16 wherein said cardiotomy reservoir and said venous reservoir have a substantially cylindrical shape having a crosswise divider which separates said substantially cylindrical shape into an upper cardiotomy chamber and a lower venous chamber and wherein said filtration means for said cardiotomy reservoir is comprised of a pleated microporous screen and said defoaming means is comprised of a foam defoamer with support means.

18. An autotransfusion unit for the collection and intravenous transfusion of cardiotomy blood, venous blood, and pleural drainage fluids having an integrally formed filtration unit and a baffle disposed therein which divides the autotransfusion unit into a separate cardiotomy reservoir, a venous blood reservoir and a filtered blood reservoir and including an integrally formed elongated vacuum regulating system separate from said cardiotomy, venous and filtered blood reservoirs including a liquid seal and a manometer for controlled vacuum regulation of suction within said cardiotomy reservoir for pleural drainage, said autotransfusion unit including a plurality of inlet and outlet ports in fluid communication with said interior reservoirs of said unit for the introduction and withdrawal of blood and body fluids into and out of said cardiotomy reservoir, said venous reservoir, and said filtered collection reservoir as well as for the introduction and withdrawal of liquids from said liquid seal and from said liquid manometer.

19. The autotransfusion unit as claimed in claim 18 wherein said cardiotomy reservoir and said venous reservoir each respectively have a top, a bottom, and sidewalls, and wherein said cardiotomy reservoir is disposed above said venous reservoir and further comprising an inlet port for venous blood disposed in the top of said autotransfusion unit for connection to a non-kinking tube exteriorly of said unit and connected to an interpassageway which passes through said cardiotomy reservoir into the upper portion of said venous reservoir and further including flow directing means disposed in the bottom of said venous reservoir for direction of blood entering said venous reservoir to the walls thereof;

and further comprising flow directing means disposed in the top of said cardiotomy reservoir for flow direction into said cardiotomy reservoir and into contact with the sidewalls thereof;

and wherein said filtered blood collection reservoir is disposed between said cardiotomy and venous reservoir chambers and said outer walls of said canister and has a bottom which slants toward a said body fluid outlet port.

20. The autotransfusion unit according to claim 19 wherein said filtration means within said cardiotomy reservoir is comprised of a pleated microporous filter and includes foam defoaming means in addition to said pleated filter.

21. A method of collecting cardiotomy and venous blood and pleural drainage fluids for autotransfusion functions respectively during and after an operating procedure comprising:

providing an autotransfusion unit for the collection and transfusion of cardiotomy blood and venous blood, and pleural drainage fluids having an integrally formed filtration unit disposed therein and a baffle which divides the autotransfusion unit into a separate cardiotomy reservoir, a venous blood reservoir, and a filtered blood reservoir and including an integrally formed elongated vacuum regulating system separate from said cardiotomy, venous and filtered blood reservoirs including a liquid seal and a manometer for controlled vacuum regulation of suction within said cardiotomy reservoir for pleural drainage, said autotransfusion unit including a plurality of inlet and outlet ports in fluid communication with said interior reservoirs of said unit for the introduction and withdrawal of blood and body fluids into and out of said cardiotomy reservoir, said venous reservoir, and said filtered collection reservoir as well as for the introduction and withdrawal of liquids from said liquid seal and from said liquid manometer;

withdrawing body fluid from a patient during an operating procedure;

delivering said body fluid to said cardiotomy reservoir and then to said filtered blood reservoir through said filtration unit;

delivering venous blood into said venous reservoir and then to said filtered blood reservoir where it is combined with fluids from said cardiotomy blood reservoir;

delivering said fluid from said filtered blood reservoir back to a patient during said operating procedure;

discontinuing withdrawing fluid from a patient and discontinuing delivering fluid to a patient after said operating procedure;

connecting said autotransfusion unit to a vacuum source through said vacuum regulating means;

withdrawing body fluids from a patient during an autotransfusion procedure by said regulated vacuum and delivering said withdrawn body fluids into said cardiotomy reservoir;

delivering said body fluid from said cardiotomy reservoir through said filtration unit to said filtered blood reservoir;

withdrawing said filtered body fluids from said filtered blood reservoir by a positive displacement pump; and, pumping said body fluids from said positive displacement pump to a patient to provide autotransfusion.

* * * * *